United States Patent [19]

Summers

[11] Patent Number: 4,609,821
[45] Date of Patent: Sep. 2, 1986

[54] TESTING FOR THE PRESENCE OF NATIVE HYDROCARBONS DOWN A BOREHOLE

[75] Inventor: Charles F. Summers, Angus, Scotland

[73] Assignee: NL Industries, Inc., New York, N.Y.

[21] Appl. No.: 608,762

[22] Filed: May 9, 1984

[30] Foreign Application Priority Data

Jul. 6, 1983 [GB] United Kingdom ................ 8318295
Apr. 19, 1984 [GB] United Kingdom ................ 8410205

[51] Int. Cl.$^4$ .............................................. G01V 5/00
[52] U.S. Cl. ................................... 250/255; 250/253; 250/301; 250/254
[58] Field of Search ................ 250/255, 301, 253, 254

[56] References Cited

U.S. PATENT DOCUMENTS

| | | | |
|---|---|---|---|
| 2,459,512 | 11/1944 | Fash et al. | 250/301 |
| 2,591,737 | 11/1950 | Souther | 250/301 |
| 3,205,353 | 9/1965 | Bray | 250/301 |
| 4,031,398 | 6/1977 | Callis et al. | 250/328 |

OTHER PUBLICATIONS

Hemphill et al., "Lab Analy. and Airborne Det. of Mat. Stimul. to Luminesse by the Sun", J. of Lum., vol. 31/32, Part II, Dec.-84, p. 724.
Czembor, R., "Fluorescence Meas. Process for Det. Small Quant. of Oil in Lyes...", JR 5/1975.

Primary Examiner—Carolyn E. Fields
Assistant Examiner—Richard Hanig
Attorney, Agent, or Firm—Browning, Bushman, Zamecki & Anderson

[57] ABSTRACT

In order to provide a reliable test for the presence of native hydrocarbons down a borehole during drilling with an oil-base drilling mud, a sample of the rock cuttings brought up from the vicinity of the drill bit by the circulating mud flow is collected, the sample or a fluid prepared from the sample is then placed in a spectrometer and is excited with electromagnetic radiation of one or more wavelengths. The radiation absorbed and/or emitted by the excited sample or sample preparation is sensed, and a plot is produced of the excitation and/or emission wavelengths against intensity, or in certain circumstances of the emission wavelengths against the excitation wavelengths. It can then be determined from the characteristic profile so obtained whether the hydrocarbon content of the sample incorporates only the oil base of the drilling mud or a combination of this oil-base and native hydrocarbons.

5 Claims, 10 Drawing Figures

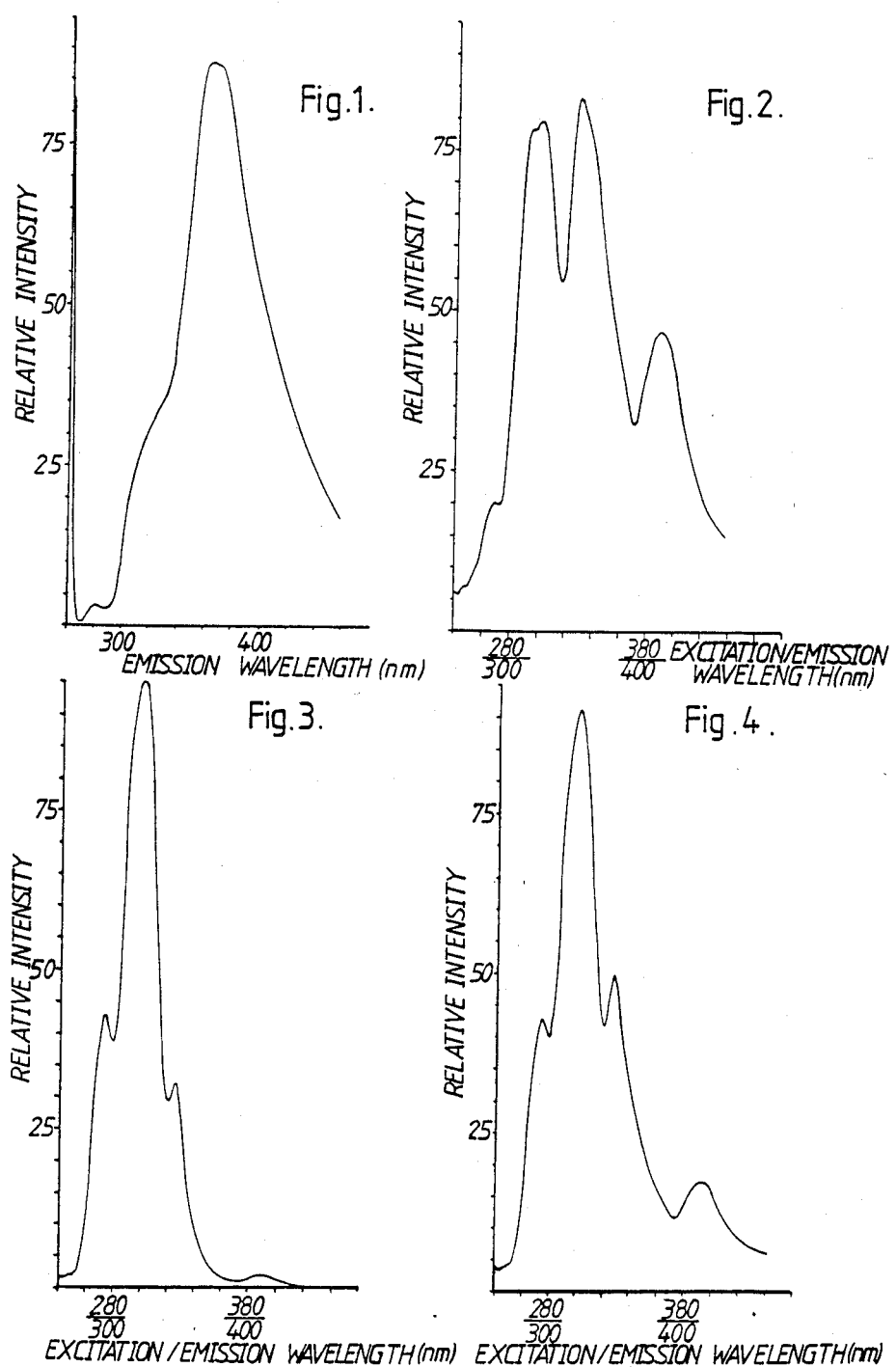

TESTING FOR THE PRESENCE OF NATIVE HYDROCARBONS DOWN A BOREHOLE

BACKGROUND OF THE INVENTION

This invention relates to the testing for the presence of native hydrocarbons down a borehole during drilling of the borehole.

It is conventional drilling practice, when hydrocarbon bearing levels are reached during the drilling of a well, to withdraw the drill string from the borehole and to run a corer down the borehole in order to withdraw a core of sample material from the bottom of the well for subsequent analysis. However, this is a time-consuming procedure and is very costly in terms of lost drilling time. In order to attempt to ensure that this procedure is not carried out erroneously before hydrocarbon bearing levels have been reached or that a hydrocarbon reservoir is not missed by coring too late, therefore, it is also the practice to collect samples of rock cuttings brought up from the vicinity of the drill bit by the circulating drilling mud flow, and to examine these in the presence of ultra-violet light. The aromatic components of native hydrocarbons flouresce strongly under ultra-violet light, that is they absorb light energy at a particular wavelength and emit light energy at a different, longer wavelength, and accordingly the particular nature of the fluorescence of the sample cuttings will indicate to a skilled observer whether the cuttings contain native hydrocarbons and thus whether the hydrocarbon bearing levels have been reached. In the event of a positive result of this test, the drill string may be withdrawn and the corer may be run down the borehole in order to confirm this result.

The above procedures have operated satisfactorily in the drilling of oil wells using conventional water-base drilling muds. However, such drilling muds are being replaced in a number of applications by oil-base drilling muds. The advantages of using oil-base drilling muds for drilling highly deviated wells in a number of fields have become widely recognised in recent years. It is possible to drill gauge holes quickly and without major problems because, among other attributes, these muds prevent hydration of shales, are stable in the presence of salts and at high temperatures and have excellent lubricating properties. As deeper and more problematic formations are investigated, oil-base muds are also becoming increasingly important in exploration drilling. Furthermore low toxic oil-base muds formulated with low aromatic base oils, instead of diesel as used in conventional oil-base muds, have been developed in response to government guidelines to the industry on the toxicity of discharges to the marine environment from offshore drilling rigs.

However, the use of diesel oil muds and low toxic oil muds alike presents difficulties in reliably testing for the presence of native hydrocarbons in the sample cuttings under ultra-violet light using the existing technique. The reason for this is that the oil base of the drilling mud also contains aromatic components which fluoresce under ultra-violet light. Under down-hole conditions mud filtrate to some extent invades the rock matrix and its presence confuses the detection of native hydrocarbons by the conventional method. The mixture of aromatic compounds contained in native hydrocarbons and drilling muds is complex, containing fluorescing species in the ultra-violet and visible parts of the spectrum. It is not unlikely that scattered and re-emitted light, which would be typically emitted in the ultra-violet at appropriate dilutions, may also be observed visually. Thus it may not be possible for an observer to distinguish between fluorescence due to the presence of the oil base of the drilling mud alone in the sample cuttings and fluorescence due to a combination of the oil base and native hydrocarbons. This is obviously highly unsatisfactory as it may lead to a false judgment that native hydrocarbons have been detected, resulting in a considerable loss of drilling time while the corer is run down the borehole, or alternatively may mean that a hydrocarbon reservoir is missed.

It is an object of the invention to develop a technique for reliably testing for the presence of native hydrocarbons during drilling with an oil-base drilling mud.

SUMMARY OF THE INVENTION

According to the invention there is provided a method of testing for the presence of native hydrocarbons down a borehole during drilling of the borehole using an oil-base drilling mud, comprising collecting a sample of rock cuttings brought up from the vicinity of the drill bit by the circulating mud flow, exciting the sample or a fluid prepared from the sample with electromagnetic radiation of one or more wavelengths, sensing the radiation absorbed and/or emitted by the excited sample or sample preparation, monitoring the excitation and/or emission wavelengths against intensity and/or monitoring the emission wavelengths against the excitation wavelengths, and determining whether the profile so obtained is characteristic of only the drilling mud or of a combination of the mud and native hydrocarbons.

In this manner a profile characteristic of the sample is obtained, and this may be compared with profiles obtained with samples known to contain native hydrocarbons of the relevant type and/or with profiles obtained with samples known not to contain native hydrocarbons. In this way it is possible to rapidly and reliably discriminate samples which contain native hydrocarbons in addition to those of the drilling mud without it being necessary to separate the different fluorescing species.

The exciting radiation may be, but is not necessarily, ultra-violet light. Furthermore the sensed radiation is preferably that which is transmitted by the sample if the sample or sample extract is transparent (transmitted fluorescence). Alternatively, if the sample or sample extract is opaque, the sensed radiation may be that which is reflected from the sample or sample extract (reflected fluorescence).

In a preferred embodiment the sample or sample preparation is excited with electromagnetic radiation such that the excitation and emission wavelengths of the sample or sample preparation are scanned a fixed wavelength interval apart, and the excitation and/or emission wavelengths are monitored against intensity so as to obtain a characteristic profile.

Such a method is particularly sensitive and reliable. This is because the wavelength shift between the excitation and emission radiation guarantees a high signal-to-noise ratio. Furthermore the described technique is highly specific and simple to use, more particularly since it is not necessary to separate the mixture of oils into separate fluorescing species.

BRIEF DESCRIPTION OF THE DRAWINGS

In order that the invention may be more fully understood, reference will now be made, by way of example, to the accompanying drawings, in which:

FIG. 1 is a plot of an emission spectrum of a crude oil obtained by a first method in accordance with the invention;

FIG. 2 is a plot of a synchronously excited emission spectrum of a crude oil obtained by a second method in accordance with the invention;

FIG. 3 is a plot of a synchronously excited emission spectrum of a pure low toxicity oil-base mud;

FIG. 4 is a plot of a synchronously excited emission spectrum of a low toxicity oil-base mud containing 2% by volume of a crude oil;

DETAILED DESCRIPTION OF THE DRAWINGS FIRST METHOD

Figure 5:
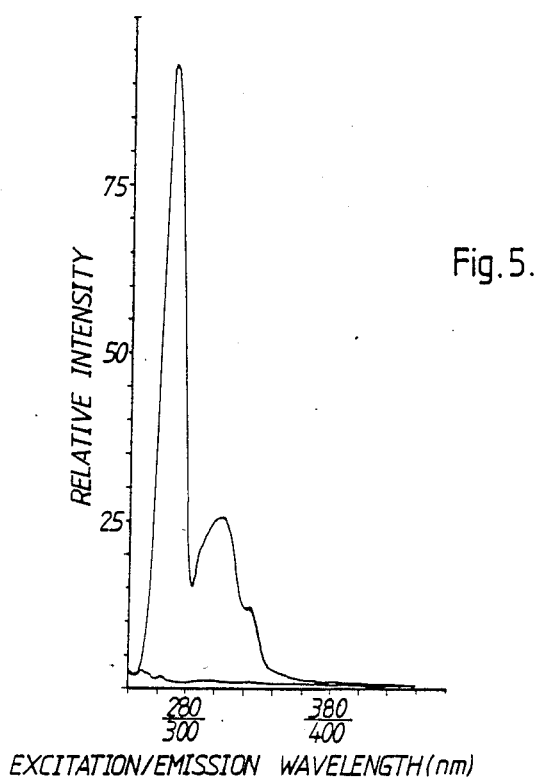
FIG. 5 is a plot of a synchronously excited emission spectrum of a gas-condensate.

In a first method in accordance with the invention the sample is subjected to so-called conventional spectroscopic techniques according to which the relative quantities of light energy from an ultra-violet source which are absorbed and/or emitted at various wavelengths in the ultra-violet and visible range are measured by means of a UV absorption spectrometer or a UV fluorescence spectrometer. The resulting absorption and emission wavelengths are plotted against intensity, as shown for example in FIG. 1 in which a plot of the emission spectrum of a North Sea crude oil excited at 259 nm is shown. However, the emission profiles of mixtures of aromatic compounds obtained by such a method are featureless and thus of little direct diagnostic value.

Nevertheless, if the identity of the mixture of hydrocarbons is known, for example if it is known which particular crude oil will be encountered in the field when drilling a particular well, it is possible to use this method to determine what proportion of the hydrocarbon mixture present in the sample cuttings is the crude oil by comparison with results obtained for a range of crude oil/oil mud mixtures studied in the laboratory.

Using UV absorption spectroscopy to illustrate this method we can define absorbance A, using the Beer Lambert Law, as:

$$A = \log\left(\frac{I_o}{I}\right) = ecl$$

where
I = intensity of transmitted light
$I_o$ = intensity of incident light
e = molar extinction coefficient
c = concentration of fluorescing species
l = pathlength of the cell Provided that e and l are known it is possible to write:

$$A = kc$$

where k is a constant

For mixtures of hydrocarbons the total absorbance $A_{tot}$ is given by the sum of the absorbances of the individual components, so that for an oil mud/crude oil mixture:

$$A_{tot} = k_1 c_{mud} + k_2 C_{oil}$$

Thus, if measurements of absorbance at two different wavelengths are made, together with an estimation of $k_1$ and $k_2$, the values of $c_{mud}$ and $c_{oil}$ may be calculated. The constant $k_1$ can be determined by making measurements on a series of solutions of oil mud of known concentrations. Similarly the constant $k_2$ can be obtained from solutions of crude oil. A plot of absorbance against concentration is required, with the slope of this plot giving the appropriate values of $k_1$ and $k_2$.

All samples are examined as fluids. Rock samples are prepared by washing (to remove oil base mud adhering to outer surfaces), crushing (to make the rock matrix contents accessible to the solvent) and solvent extraction (vigorous agitation in a suitable solvent, for example dichloromethane or cyclohexane, to take the matrix contents into solution). Fluid samples must be sufficiently dilute to avoid artefacts caused by concentration, for example energy transfer between adjacent fluorescing species changing the distribution of emission wavelengths, but sufficiently concentrated to avoid a significant background contribution from the solvent.

SECOND METHOD

In a second method in accordance with the invention the sample is subjected to so-called synchronous scanning spectroscopy according to which, instead of scanning the emission/excitation spectrum at a fixed excitation/emission wavelength, as in the first method described above, the excitation and emission wavelengths are scanned simultaneously a fixed wavelength interval apart. This has the effect of creating a small spectral "window" in which the fluorescing components of the mixture are successively excited throughout the wavelength range. The improvement in the resolution of detailed features in the emission spectra generated by this technique is dramatic and can be exploited to provide a unique 'fingerprint' of aromatic mixtures. The crude oil whose emission profile is illustrated in FIG. 1 is characterised by a synchronously excited emission spectrum in FIG. 2.

In use of this method in the field to determine when oil-bearing levels have been reached during drilling, rock cuttings are periodically collected from a double decker shale shaker through which the drilling mud which has travelled up the drill pipe from the vicinity of the drill bit is passed prior to being recirculated. Simultaneously a mud sample is collected from immediately upstream of the shale shaker. At each periodic collection a sample is prepared from the cuttings in the manner described above with reference to the first method, and optionally both the rock sample and the mud sample are subjected to high pressure filtration or centrifugation prior to further dilution in a suitable solvent. Dilution rates vary according to the amount of aromatics in the sample. Typically crude oil is diluted to $1:10^5$, low toxicity oil-base mud to $1:10^4$ and rock samples to $1:10^3$. The rock sample, the mud sample and a solvent blank are then run as a group in the spectrometer, and the resulting emission profiles are automatically generated by a chart recorder. Visual inspection and comparison of these profiles reliably indicates when the collected rock cuttings are characteristic of oil-bearing levels having been reached.

Using this method for quantifying the presence of a known crude oil in a mud/hydrocarbon mixture, in the major region of interest, that is in the range where both the mud and the crude oil fluoresce, the intensity $I(\lambda'\lambda)$ at particular emission and excitation wavelengths $\lambda$ and $\lambda'$ is given by:

$$I_s(\lambda'\lambda) = KcdE_x(\lambda')E_m(\lambda) \quad (1)$$

where
K = an experimental constant
c = concentration of the analyte
d = path length of the cell
$E_x(\lambda')$ = intensity distribution of the excitation spectrum
$E_m(\lambda)$ = intensity distribution of the emission spectrum Equation (1) can be simplified to:

$$I_s(\lambda'\lambda) = xc \quad (2)$$

where $x = KdE_x(\lambda)$

For a mud/crude oil mixture $$I_s(\lambda'\lambda) = I_{oil}(\lambda'\lambda) + I_{mud}(\lambda'\lambda) \quad (3)$$

A particular synchronously excited emission spectrum may be characterised by its peaks. For example, in the case of the crude oil emission spectrum shown in FIG. 1, there are four peaks of interest occurring at 270/290 nm, 300/320 nm, 330/350 nm and 390/410 nm respectively. In the case of a mud/crude oil mixture, therefore, the intensity $I_i$ at peak (i) may be expressed as:

$$I_i = a_i c_{oil} + b_i c_{mud} \quad (4)$$

where
$a_i$ = proportionality constant of the crude oil at wavelength i
$b_i$ = proportionality constant of the mud at wavelength i
i = a specified wavelength This method requires the evaluation of $a_i$ and $b_i$ for each value of i. Calculation of a and b requires accurate measurements of the fluorescence intensity of solutions of mud and oil of known concentrations. The values of $I_s$ obtained from the crude oil and mud solutions can then be plotted on separate graphs. The values of $a_i$ can be obtained from the slopes of the lines from the crude oil solution data. The values of $b_i$ can be obtained from the corresponding data from the mud solutions. In all cases these lines should pass through zero. For this type of analysis the fluorescence 'fingerprint' of the crude oil must be known. Alternatively, it is necessary to simulate an 'average' crude oil or obtain average values of $a_i$.

The second method may also be used in exploration drilling where, by definition, the occurrence and identity of native hydrocarbons is unknown. In this case, therefore, it is more important to distinguish between the drilling mud and other hydrocarbon mixtures than to give a quantitative estimate of any crude oil present. In this context conventional spectroscopy is inappropriate but synchronous scanning allows samples to be rapidly 'fingerprinted' at the well site. During the drilling of a well, the emission spectra of the mud and of the sample cuttings will be virtually indistinguishable in the absence of native hydrocarbons. However, in the presence of a crude oil, the cuttings profile will show a shift away from the mud profile and toward that of the crude oil present in the rock matrix. The process can be simulated experimentally to demonstrate the sensitivity of the technique. FIGS. 3 and 4 illustrate the effect of adding 2% by volume of a North Sea crude oil to a low toxicity oil-base mud, FIG. 3 showing the synchronously excited emission spectrum of the pure mud and FIG. 4 showing the corresponding spectrum of the mud to which the crude oil has been added. The increase in luminescence at 330/350 nm and at 390/410 nm caused by the addition of the crude oil and the diminution of relative intensity at 270/290 nm is immediately apparent. So long as any surface treatment of the mud, which could affect its luminescence characteristics, is closely monitored, it should normally be possible by this method to detect small scale changes in the emission profiles of cuttings, cores and other down-hole samples during exploration drilling which are attributable to native hydrocarbons.

It should be appreciated that the emission wavelength of aromatic compounds increases in approximate proportion to the number of ring structures in the molecule. Typically, the emission spectrum of an oil, such as that of FIG. 1, is characterised by longer wavelength fluorescence attributable to polynuclear aromatics, while the emission spectrum of a gas-condensate, which contains principally low ring number aromatics, is characterised by fluorescence at shorter wavelengths, an example of such a spectrum being shown in FIG. 5 for a North Sea condensate. Both diesel-base mud and low toxicity oil-base mud profiles occupy an intermediate position between these two extremes although, quantitatively, diesel is richer in aromatics than the base oils used in low toxicity muds.

Figure 6:
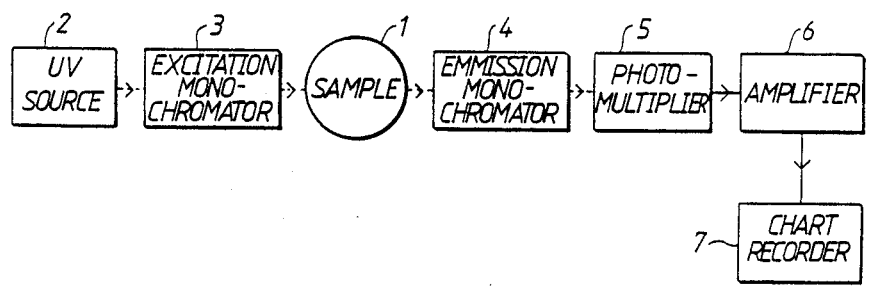
FIG. 6 is a simplified block diagram of apparatus which may be used in the second method.

The apparatus of FIG. 6 may be used to analyse the synchronously excited emission spectrum of a sample 1 prepared by the process described above with reference to the first method. The apparatus comprises an ultraviolet source 2 for providing a beam of pulsed radiation for exciting the sample 1, an excitation monochromator 3 and an emission monochromator 4 for selecting the wavelengths at which absorption and fluorescence are to be measured, a photomultiplier 5 for detecting the emitted radiation, an amplifier 6 and a chart recorder 7 or other means for recording the profiles. In use the excitation and emission monochromators 3 and 4 are caused, possibly under computer control, to scan simultaneously a fixed wavelength increment $\Delta\lambda$ apart. The resulting emission wavelengths are plotted against intensity by the chart recorder 7. Characteristic differences between synchronous excitation/emission spectra of sample mixtures may be optimised by varying the wavelength increment between excitation and emission scans.

Figure 7:
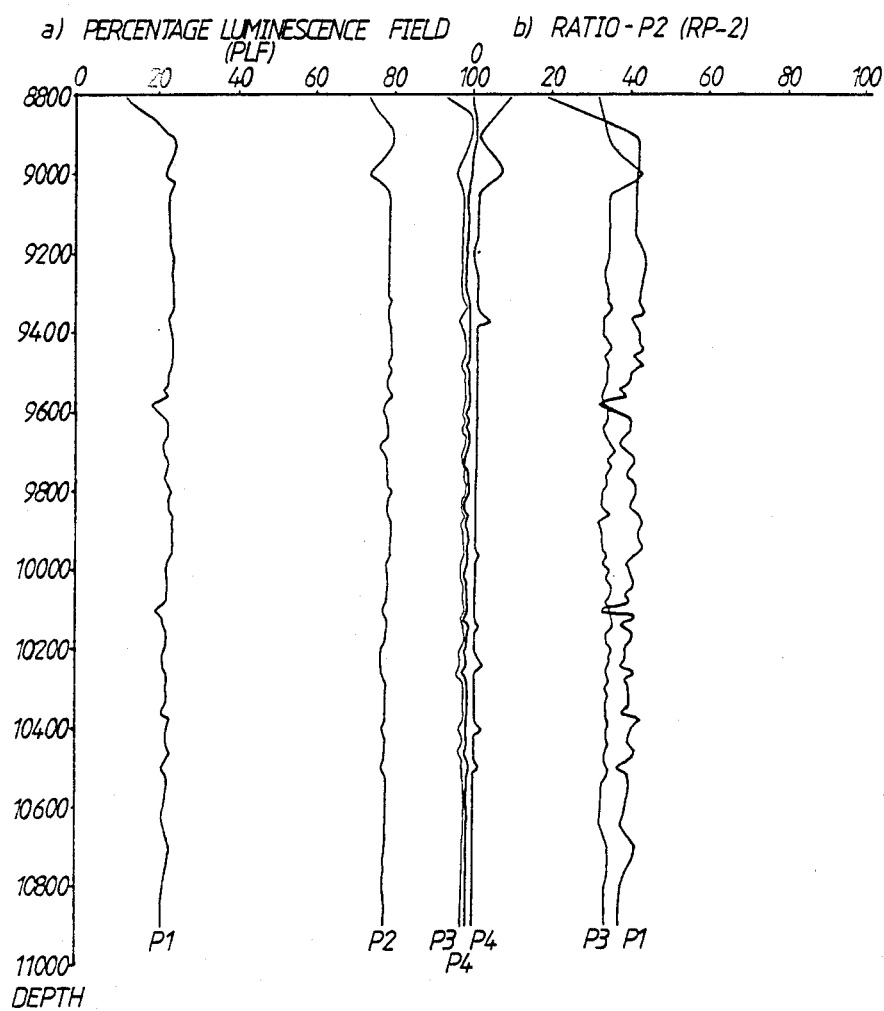
FIGS. 7 and 8 show luminescence logs of mud and sample cuttings respectively against depth.
Figure 8:
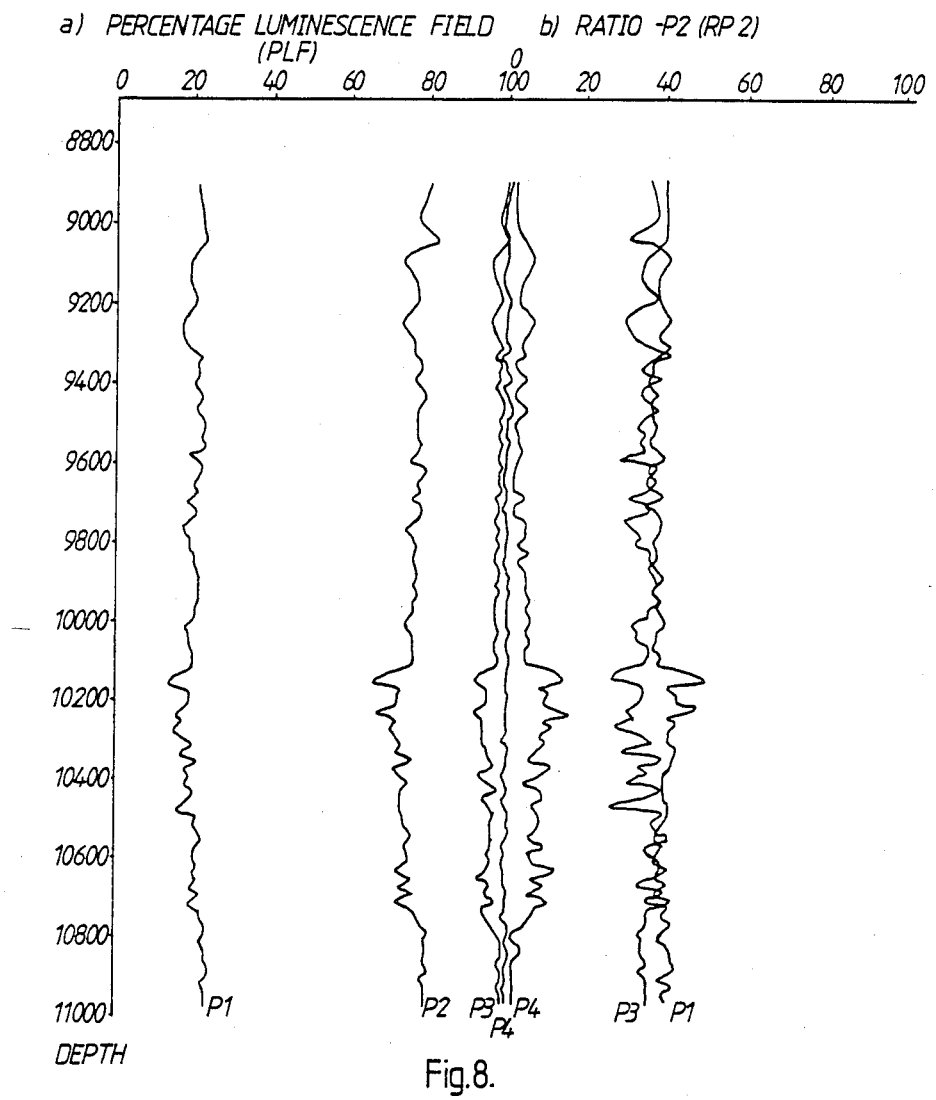

It is usual for drilling parameters to be logged against depth for post well evaluation. In order that the luminescence characteristics of the mud and sample cuttings may be logged against depth it is necessary to transform the data. One method of doing this is to measure the relative intensity of the peaks in each profile and express these values either (a) as a percentage of the total luminescence or (b) as a ratio in relation to a particular peak. FIG. 7 shows a luminescence log of a mud and FIG. 8 shows a luminescence log of corresponding sample cuttings from a North Sea well, both logs showing the intensity of the peaks both (a) as percentages of the total luminescence and (b) as ratio transformations relative to a peak P2. These logs allow lithology and other drilling parameters to be correlated with the occurrence of native hydrocarbons as indicated by the above described synchronous scanning method.

Notwithstanding what is said above, it is possible to obtain quantitative information from the above described synchronous scanning method by introducing into the mud a marker which fluoresces outside the wavelength region in which the mud and native hydrocarbons typically fluoresce. At the wavelength at which the marker fluoresces $\lambda_m$ its fluorescence intensity $I_m$ will be given by:

$$I_m = I_{mud} = b_m c_{mud} \tag{5}$$

where $b_m$ = proportionality constant for the marker

Using this relationship and equation (4) above it is possible to write:

$$\frac{I_i}{I_m} = \frac{a_i c_{oil} + b_i c_{mud}}{b_m c_{mud}} \tag{6}$$

Therefore the concentration of crude oil is given by:

$$c_{oil} = \left\{ \frac{b_m c_{mud} I_i}{I_m} - b_i c_{mud} \right\} / a_i \tag{7}$$

THIRD METHOD

Figure 9A:
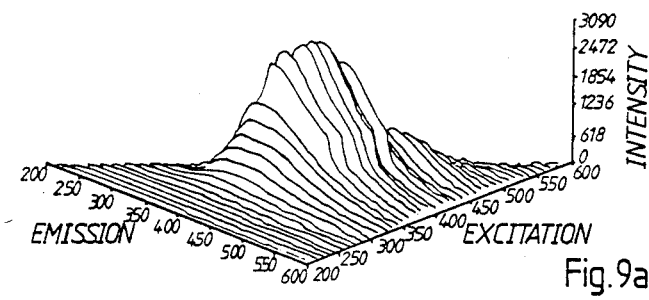
FIG. 9 shows a three-dimensional diagram and a contour map of emission spectra of a typical oil.
Figure 9B:
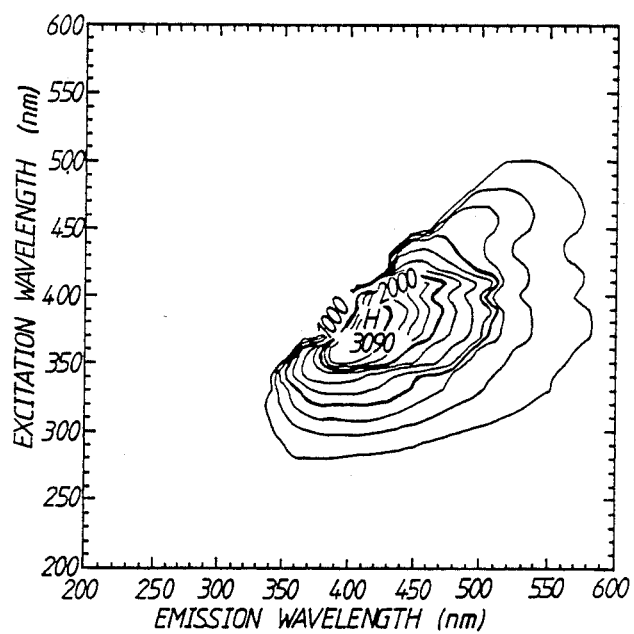

The methods so far described only sample the emission surface of a fluorescing mixture. Because of the subjective element implied in the choice of excitation and emission wavelengths and of wavelength increments, it is possible that not all of the usable information about the emission surface is revealed. In a further method, which may be referred to as total luminescence spectroscopy, therefore, an emission spectrum is examined at a number of fixed excitation wavelengths and the resulting emission profiles are supplied to a computer, interfaced with the spectrometer, which stores and processes the data points to produce a representation of relative intensity as a function of both excitation and emission wavelengths. The resulting representation of the emission surface may be plotted either as a three-dimensional diagram (FIG. 9a) or as a contour map (FIG. 9b). The contour map of the fluorescence surface reveals the full register of fluorescence information available from the sample and is, therefore, the most powerfully diagnostic of the methods described here.

In the above described methods sample examination is made using transmitted light and this requires a solvent extraction and dilution treatment to obtain a transparent medium. However, reflection fluorescence can also be used to distinguish between muds and native hydrocarbons, although the characteristic peaks of the major components do not occur at the same wavelengths as those obtained using transmitted fluorescence. Nevertheless reflection fluorescence enables opaque liquids to be investigated by surface reflection by incorporating in the spectrometer a front surface accessory which is angled to the light source so as to obtain a optimum signal-to-noise-ratio.

I claim:

1. A method of testing for the presence of native hydrocarbons down a borehole during drilling of the borehole using an oil-base drilling mud, comprising collecting a sample of rock cuttings brought up from the vicinity of the drill bit by the circulating mud flow, exciting the sample or a fluid prepared from the sample with electromagnetic radiation and sensing the radiation emitted by the excited sample or sample preparation, such that the excitation and emission wavelengths of the sample or sample preparation are scanned a fixed wavelength interval apart, monitoring the excitation and/or emission wavelengths against intensity, and determining whether the profile so obtained is characteristic of only the drilling mud or of a combination of the mud and native hydrocarbons.

2. A method according to claim 1, wherein the exciting radiation is ultra-violet light.

3. A method according to claim 1, wherein the concentration of a known native hydrocarbon in the sample or sample preparation is determined from its characteristic profile and from constants obtained from profiles characteristic of solutions of drilling mud of known concentration and from profiles characteristic of solutions of the known native hydrocarbons of known concentration.

4. A method according to claim 1, wherein a sample or sample preparation is obtained at a plurality of depths within the borehole, each sample or sample preparation is separately excited so as to obtain its characteristic excitation or emission profile, and the relative intensities of the peaks within these profiles are logged against depth.

5. A method according to claim 1, wherein a marker which absorbs or emits radiation at a known wavelength is incorporated in the drilling mud and the concentration of a native hydrocarbon in the sample or sample preparation is determined from its characteristic profile and from the intensity of the radiation absorbed or emitted when the mud is excited at said known wavelength.

* * * * *